(12) United States Patent
Kowalchuk et al.

(10) Patent No.: US 12,708,558 B2
(45) Date of Patent: Aug. 18, 2026

(54) TEMPERATURE THERAPY GARMENT AND METHOD

(71) Applicants: Jason Ronald Kowalchuk, London (CA); Luisa Beer, London (CA)

(72) Inventors: Jason Ronald Kowalchuk, London (CA); Luisa Beer, London (CA)

( * ) Notice: Subject to any disclaimer, the term of this patent is extended or adjusted under 35 U.S.C. 154(b) by 201 days.

(21) Appl. No.: 18/586,200

(22) Filed: Feb. 23, 2024

(65) Prior Publication Data

US 2025/0268746 A1 Aug. 28, 2025

(51) Int. Cl.
*A61F 7/02* (2006.01)
*A61F 5/30* (2006.01)

(52) U.S. Cl.
CPC .................. *A61F 7/02* (2013.01); *A61F 5/30* (2013.01); *A61F 2007/0219* (2013.01); *A61F 2007/0234* (2013.01); *A61F 2007/0236* (2013.01)

(58) Field of Classification Search
CPC ........ A61F 7/02; A61F 7/0219; A61F 7/0234; A61F 7/0236
See application file for complete search history.

(56) References Cited

U.S. PATENT DOCUMENTS 3,246,337 A 4/1966 Copeland
3,950,789 A 4/1976 Konz et al.
5,146,625 A 9/1992 Steele et al.
5,484,448 A 1/1996 Steele et al.
6,931,875 B1 8/2005 Allen et al.
8,449,588 B2 5/2013 Horn
8,585,746 B2 11/2013 Ilcheva et al.
9,717,287 B2 8/2017 DiBernardo et al.
11,684,094 B2 6/2023 Arnold et al.
2006/0064147 A1 3/2006 Almqvist
2013/0131764 A1 5/2013 Grove
2013/0204332 A1 8/2013 Amalfi
2016/0113812 A1 4/2016 Bender
2017/0181887 A1 6/2017 Gentile
2023/0329366 A1 10/2023 Blakely et al.
2025/0160450 A1* 5/2025 Bond ................ A41D 13/0015

FOREIGN PATENT DOCUMENTS

WO 03061412 A2 7/2003

OTHER PUBLICATIONS

ComfiTech Amazon Store (online: https://www.amazon.ca/stores/ComfiTECH/page/D88FD636-17BF-419B-9E64-E791623019C3?ref_=ast_bln).
ComfiTech Amazon Store, https://www.amazon.ca/Comfitech-Headache-Migraine-Wearable-Compress/dp/BOBPLVPVYL?ref_=ast_sto_dp&th=1.

(Continued)

*Primary Examiner* — Joseph A Stoklosa
(74) *Attorney, Agent, or Firm* — Smart & Biggar LP

(57) ABSTRACT

A cold therapy garment formed from one or more clothing panels. Each clothing panel extends from a first edge to a second edge opposite the first edge and includes an integrated flexible gel sheet to be cooled prior to a user wearing the cold therapy garment, each integrated flexible gel sheet extending continuously across the clothing panel from the first edge to the second edge, and each integrated flexible gel sheet formed of a cold-therapy material having a semi-rigid form throughout a selected temperature use range.

15 Claims, 8 Drawing Sheets

(56) References Cited

OTHER PUBLICATIONS

ComfiTech Amazon Store, https://www.amazon.ca/ComfiTECH-Reusable-Cervical-Compress-Injuries/dp/B096JNNFCW?ref_=ast_sto_dp&th=1.
ComfiTech Amazon Store, https://www.amazon.ca/ComfiTECH-Migraine-Headache-Cervical-Recovery/dp/B0C7QSYCW7/ref=asc_df_B0BYNLLLCJ/?tag=googleshopc0c-20&lin%E2%80%A6.
ComfiTech Amazon Store, https://www.amazon.ca/ComfiTECH-Tendonitis-Compression-Injuries-Reusable/dp/B096WXPFTT?ref_=ast_sto_dp&th=1.
Canadian Intellectual Property Office: Written Opinion of the International Searching Authority, dated May 22, 2025, for PCT Patent Application Serial No. PCT/CA2025/050125.

* cited by examiner

TEMPERATURE THERAPY GARMENT AND METHOD

TECHNICAL FIELD

The disclosure relates to temperature therapy, and particularly to a temperature therapy garment.

BACKGROUND

Temperature therapy has been used for many years. For example, ice baths are used to reduce the skin temperature of a user. The user may immerse a substantial portion of their body in cold water for at least a few minutes to reduce their skin temperature. The water of the ice bath may also apply pressure to the user's body to force blood towards the core of the user's body.

Setting up temperature therapy can be difficult. For example, an ice bath typically requires a vessel large enough to hold substantially all of the user's body, enough water to fill the vessel, and enough ice to cool the water and maintain a cold water temperature throughout the bath. Efforts have been made to improve the user experience. For example, inflatable ice vessels have been developed to reduce the storge space needed for the vessel and chiller devices have been developed to cool the water of the bath without the need to produce and add ice.

However, there remains a need for improved temperature therapy apparatus and methods.

SUMMARY

According to an aspect, there is provided a cold therapy shirt, comprising: a plurality of clothing panels forming a torso portion and first and second arms, the first and second arms each joined at upper ends thereof to the torso portion, and wherein each clothing panel extends from a first edge to a second edge opposite the first edge and each clothing panel includes an integrated flexible gel sheet to be cooled prior to a user wearing the cold therapy shirt, each integrated flexible gel sheet extending continuously across the clothing panel from the first edge to the second edge, and each integrated flexible gel sheet formed of a cold-therapy material having a semi-rigid form throughout a selected temperature use range.

In some examples, the cold therapy material is a hydrogel.

The selected temperature use range may be a range of 3 degrees Celsius to 20 degrees Celsius.

The plurality of clothing panels may include a first panel extending at least from a torso right side to a torso left side, and the continuous sheet of cold therapy material of the first panel also extends at least from the torso right side to the torso left side.

The first panel may extend at least from a lower end of the torso portion to an upper end of the torso portion, and the continuous sheet of cold therapy material of the first panel also extends at least from the lower end of the torso portion to the upper end of the torso portion.

The first panel may be a rear torso panel and the first edge is at a torso right side seam and the second edge is at a torso left side seam.

Each panel may comprise the sheet of cold therapy material enclosed between layers of fabric.

The cold therapy shirt may be sized and shaped to compress a torso and arms of the user. The plurality of clothing panels may be joined to one another using stretch stitching.

According to another aspect, there is provided cold therapy pants, comprising: one or more clothing panels forming first and second legs, the first and second legs joined at upper ends thereof via a waist portion, and wherein each clothing panel extends from a first edge to a second edge opposite the first edge and each clothing panel includes an integrated flexible gel sheet to be cooled prior to a user wearing the cold therapy pants, each integrated flexible gel sheet extending continuously across the clothing panel from the first edge to the second edge, and each integrated flexible gel sheet formed of a cold-therapy material having a semi-rigid form throughout a selected temperature use range.

In some examples, the one or more clothing panels includes a first panel, the first panel extending at least from a right side of one of the first and second legs to a left side of the one of the first and second legs, and the continuous sheet of cold therapy material of the first panel also extends at least from the right side of the one of the first and second legs to the left side of the one of the first and second legs.

The first panel may also extend at least from a lower end of the one of the first and second legs to the upper end of the one of the first and second legs, and the continuous sheet of cold therapy material of the first panel also extends at least from the lower end of the one of the first and second legs to the upper end of the one of the first and second legs.

The one or more clothing panels may include a plurality of clothing panels, and the first panel is a front panel and the first edge is at an inseam and the second edge is at an outseam.

Each panel may comprise the sheet of cold therapy material enclosed between layers of fabric.

The cold therapy pants may be sized and shaped to compress legs of the user. The one or more clothing panels may include a plurality of clothing panels joined to one another using stretch stitching.

According to another aspect, there is provided a method of cold therapy, comprising: cooling a cold therapy material in at least one cold therapy garment, the cold therapy material having a semi-rigid form throughout a selected temperature use range, the at least one cold therapy garment formed from one or more clothing panels, each clothing panel extending from a first edge to a second edge opposite the first edge and including a continuous flexible gel sheet formed of the cold-therapy material, each continuous flexible gel sheet extending across the panel from the first edge to the second edge; donning, after cooling the cold therapy material, the at least one cold therapy garment whereby the at least one cold therapy garment overlies at least 30% of a surface area of a wearer's body; wearing, after donning the at least one cold therapy garment, the at least one cold therapy garment for a period of time whereby a skin temperature of the wearer is decreased to a decreased temperature.

In some examples, the at least one cold therapy garment includes a cold therapy pants comprising first and second legs joined at upper ends thereof via a waist portion, the first and second legs formed from the one or more clothing panels.

The at least one cold therapy garment may be a plurality of cold therapy garments and further include a cold therapy shirt comprising a torso portion and first and second arms, the first and second arms each joined at upper ends thereof to the torso portion, the first and second arms and the torso portion formed from the clothing panels, and wherein donning the at least one cold therapy garment includes donning the cold therapy pants and the cold therapy shirt whereby the plurality of cold therapy garments overlies at least 60% of a surface area of the wearer's body.

Each of the at least one cold therapy garment may be a compression garment sized and shaped to compress an underlying body of the wearer.

BRIEF DESCRIPTION OF THE DRAWINGS

The drawings included herewith are for illustrating various examples of systems, methods, and apparatus of the present specification. In the drawings.

DETAILED DESCRIPTION

Various apparatus or processes will be described below to provide an example of each claimed embodiment. No example described below limits any claimed embodiment and any claimed embodiment may cover processes or apparatuses that differ from those described below. The claimed embodiments are not limited to apparatuses or processes having all of the features of any one apparatus or process described below or to features common to multiple or all of the apparatus or processes described below.

Figure 1:
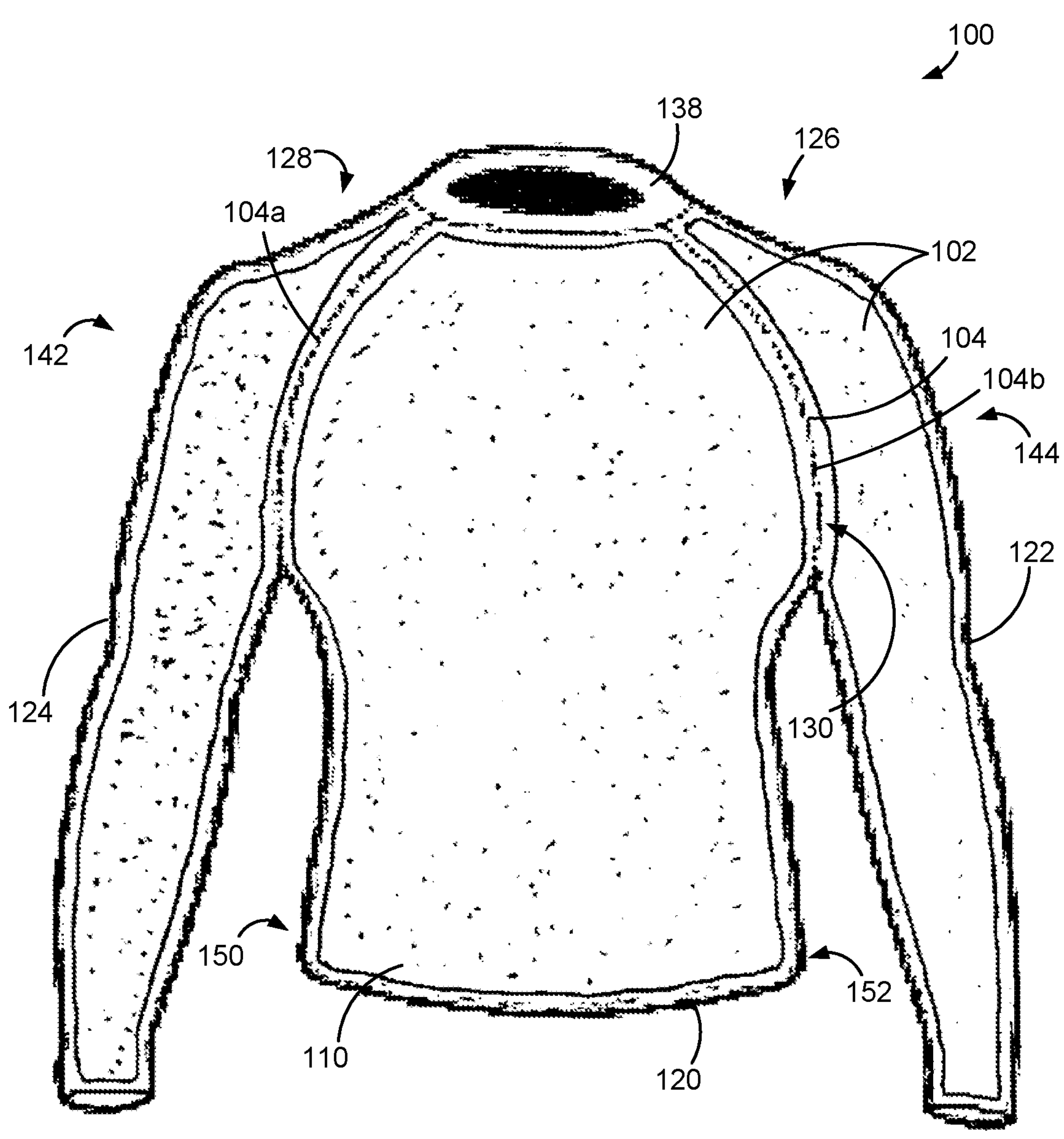
FIG. 1 is a front view of a temperature therapy shirt, according to an embodiment.
Figure 2:
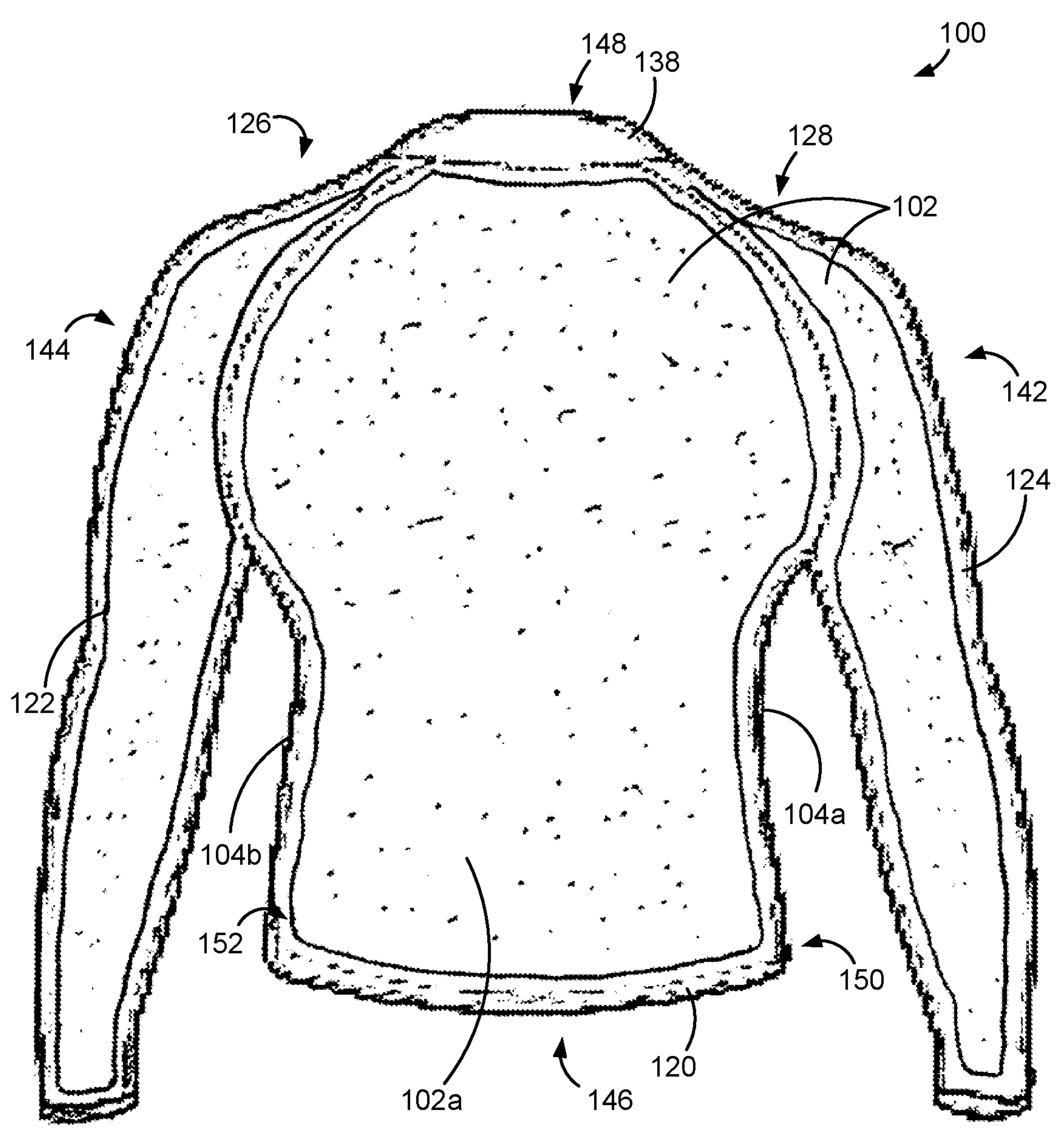
FIG. 2 is a rear view of the temperature therapy shirt of FIG. 1.

Referring now to FIGS. 1 and 2, illustrated therein is an exemplary temperature therapy garment 100. A temperature therapy garment is heatable or coolable to be subsequently worn by a wearer to warm or cool, respectively, the wearer. The temperature therapy garment 100 is designed to simulate water therapy. For example, in cold water therapy, a user submerges at least a substantial portion of the user's body in cold water. The user may submerge at least 30% of their body (e.g., their lower body from about the waist down). The user may submerge at least 60% of their body (e.g., their lower body along with much of their torso and arms). A user may enjoy a temperature therapy treatment. The cold temperatures may help centralize blood flow into the core of the user's body. The warm temperatures may help with circulation in the user's body.

The temperature therapy garment 100 simulates water therapy by overlying a substantial part of the user's body (e.g., at least 30%) with a temperature therapy material. The temperature therapy material is integrated into the garment to overly the user's body when the garment is worn. In use, the garment 100 is cooled (e.g., placed in a refrigerator or freezer or left outside during cold weather) or heated (e.g., placed in a microwave for a few seconds) and then donned by the wearer. In use, a cold therapy treatment using temperature therapy material overlying a substantial portion of the user's body (e.g., at least 30% or at least 60%) may result in brown fat activation, dopamine spikes (e.g., up to 250%), improved blood circulation and oxygen levels in the body (e.g., for easier waste and toxin removal from the body resulting in healthier organs, muscles and tissues).

Overlying a substantial portion of the user's body result in benefits that cannot be achieved through localized temperature treatment. For example, localized cold therapy may reduce inflammation and pain, but cannot achieve benefits from near full body cold exposure (e.g., as in ice bathing or cryotherapy).

The temperature therapy material integrated into the garment is formed into one or more flexible gel sheets. The sheet(s) of temperature therapy material have a semi-rigid form within an expected temperature use range. In some examples, the gel sheets of temperature therapy material are soft gel sheets within an expected temperature use range. In some examples, the temperature therapy material is a hydrogel. In some examples, the gel includes a polymer network. The expected temperature use range includes the range of temperatures from a temperature the garment is at while being prepared for use (e.g., a refrigerator temperature) to a room temperature. For a cold therapy material, the expected temperature use range may be between −20 and 30 degrees Celsius, −5 degrees Celsius and 30 degrees Celsius, −5 degrees Celsius and 25 degrees Celsius, −5 degrees Celsius and 20 degrees Celsius, 0 degrees Celsius and 20 degrees Celsius, or 3 degrees Celsius and 20 degrees Celsius. In some examples (e.g., when using certain freezers), when the material is prepared for use, a cold therapy material is expected to be cooled to between −40 and −1 degrees Celsius, −30 and −10 degrees Celsius, or −25 and −15 degrees Celsius, and so these temperatures are part of the expected temperature range. For a hot therapy material, the expected temperature use range may be between 15 degrees Celsius and 50 degrees Celsius, between 20 degrees Celsius and 45 degrees Celsius, or between 20 degrees Celsius and 40 degrees Celsius. It will be appreciated that the temperature therapy material may also be in the semirigid gel form outside the expected temperature use range.

The temperature therapy garment 100 includes one or more temperature therapy clothing panels 102. Each panel 102 includes a sheet of the temperature therapy material. The sheet of temperature therapy material extends across substantially all of the panel 102, e.g., to provide a generally continuous coverage of the temperature therapy material over the body of the wearer. It will be appreciated that a temperature therapy clothing panel having a sheet of temperature therapy material extending across all of the panel may still include a short extent beyond the sheet of temperature therapy material, e.g., to facilitate joining the panel to an adjacent panel.

In some embodiments, a single panel 102 may be shaped into a garment. In other words, the garment may include only a single panel 102 shaped into a garment (e.g., forming one or more sleeves to receive arms or legs). However, in some embodiments the garment 100 includes a plurality of panels 102, e.g., for ease of manufacturing. In embodiments which the garment 100 includes more than one panel 102, panels 102 are joined to one another at edges 104 thereof. The panels 102 may be joined in any suitable way, such as by stitching or welding panels to one another. In some embodiments, the sheet of temperature therapy material extends up to the edge of the panel 102 to provide a generally continuous layer of the temperature therapy material overlying the wearer.

Figure 3:
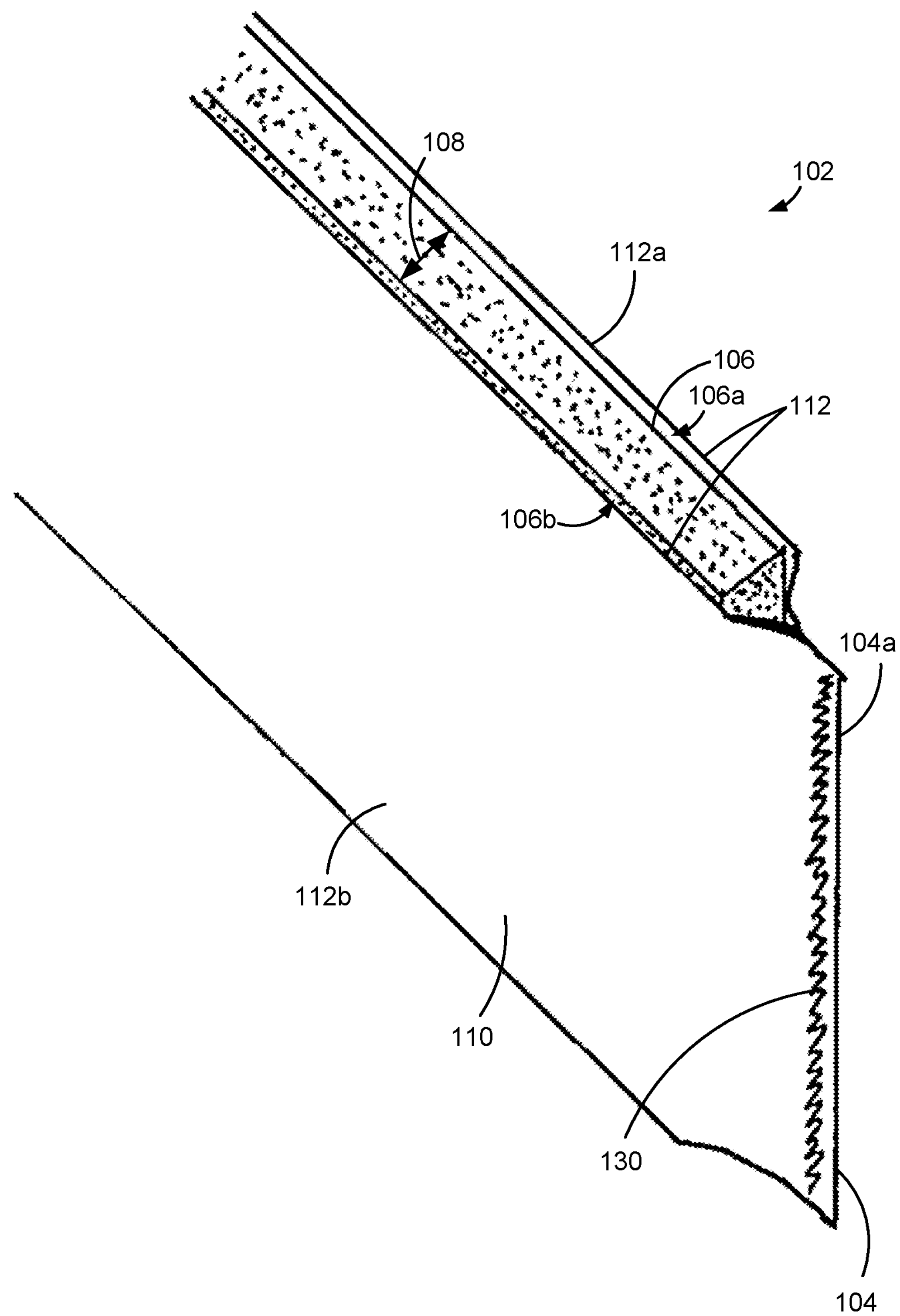
FIG. 3 is a perspective cross sectional view of a clothing panel of the temperature therapy shirt of FIG. 1.

Referring now to FIG. 3, illustrated therein is a cross sectional view of an exemplary temperature therapy clothing panel 102. The temperature therapy clothing panel 102 includes a sheet 106 of a temperature therapy material. The sheet 106 is a continuous sheet of temperature therapy material to provide a generally continuous coverage of temperature therapy material to the underlying body of the wearer when the garment is worn. The exemplary sheet 106 of temperature therapy material of FIG. 3 extends across substantially all of the panel 102 up to the edge 104 of the panel 102. The exemplary panel 102 of FIG. 1 extends from a first edge 104*a* to a second edge 104*b*, and, as illustrated in FIG. 3, the exemplary sheet 106 extends across the panel 102 from the first edge to 104*a* the second edge 104*b*. In some examples, the sheet 106 is of a generally constant thickness across the panel 102. The thickness 108 of the sheet 106 may be between 1 mm and 15 cm, between 1 mm and 10 cm, or between 1 mm and 5 cm.

The sheet 106 of temperature therapy material is integrated into the panel 102. To cool or warm the temperature therapy material, the whole garment is cooled or warmed, rather than removing the temperature therapy material from the garment for cooling or warming. In some embodiments, the panel 102 includes a cover 110 enclosing the sheet 106. The cover may protect the sheet 106 from damage and/or prevent direct user contact with the sheet 106 (e.g., from the sticky surfaces of the sheet if the sheet is formed of a sticky gel). The cover 110 permanently encloses the sheet 106. The exemplary cover 110 of FIG. 3 includes fabric 112 enclosing the sheet 106. The fabric 112 encases the sheet 106. In some embodiments, the panel 102 includes an inner layer of fabric 112*a* and an outer layer of fabric 112*b* sandwiching the sheet 106. The exemplary fabric layers 112*a*, 112*b* of FIG. 3 are stitched together to encase the sheet 106 of temperature therapy material. In other embodiments in which the cover 110 includes fabric, the fabric may be secured in other ways in addition to or in alternative to stitching (e.g., welding).

In some examples, the panel 102 is constructed to encourage easy thermal transfer from the sheet to an interior of the garment. In some examples, the cover 110 includes only a single layer over an inner side 106*a* of the sheet 106. In some examples, the panel 102 includes only the single layer of the cover between the inner side 106*a* of the sheet 106 and an interior of the garment. A single layer reduces thermal insulation to allow easier heat transfer. In some examples, the cover 110 includes a single layer on each of the inner side 106*a* and an opposite outer side 106*b* of the sheet 106. The exemplary cover 110 of FIG. 3 includes a single layer of fabric 112 on each side of the sheet 106.

However, it will be appreciated that in some examples, the panel 102 and/or the cover 110 may include more than one layer on one or both sides of the sheet 106. In some examples, an exterior side 106*b* of the garment is insulated to reduce thermal transfer between the exterior side 106*b* of the sheet and exterior of the garment. The panel 102 may include an insulating layer over the outer side 106*b* of the sheet 106 in addition to a layer of the cover 102 (e.g., in addition to the outer fabric layer 112*b*). In some examples, an additional garment may be worn over the garment 100 (e.g., a coat worn over the garment 100) to reduce heat transfer from an exterior environment to the sheet 106.

Figure 4:
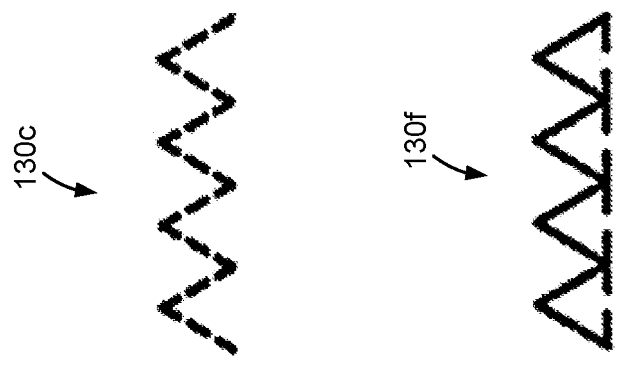
FIG. 4 is a diagram of stretch stitching examples.
Figure 4:
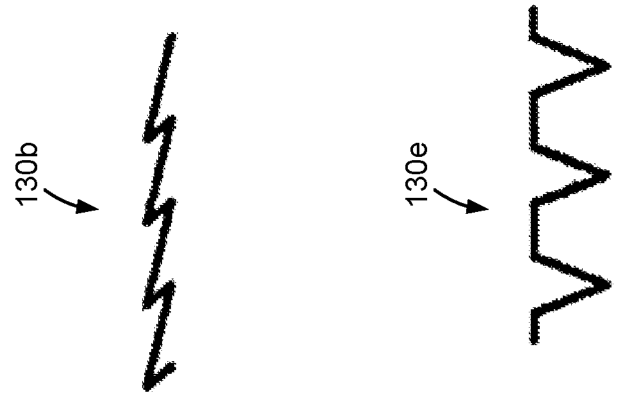
Figure 4:
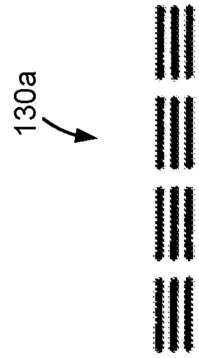
Figure 4:
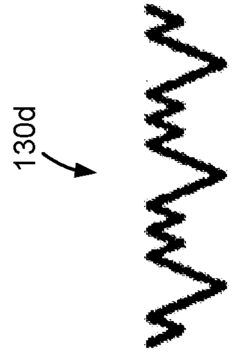
Figure 4:

Referring again to FIGS. 1 and 2, in some embodiments the garment 100 is a compression garment. A compression garment may help keep the temperature therapy material close to the wearer's skin. A compression garment may also help centralize blood flow to the core of the user's body. Compression simulates hydrostatic pressure acting upon a user during a temperature therapy bath. A compression garment fits snugly and has elastic properties. The garment 100 is sized and shaped to compress an underlying body part of a user. In some examples, the garment 100 also includes stretch stitching. The exemplary garment 100 of FIG. 1 includes stretch stitching 130 to join panels 102 to one another. The exemplary panel 102 of FIG. 3 includes stretch stitching 130 to join the upper and lower layers of fabric 112*a*, 122*b* together to enclose the sheet 106. In some examples, the same stitching may be used to close a cover 110 of a panel 102 and to join panels 102 to one another. Any suitable stretch stitching may be used to allow the compression garment 100 to stretch. Referring to FIG. 4, stretch stitching 130 may be or include, e.g., triple stretch stitching 130*a*, stretch zigzag stitching 130*b*, elastic stitching 130*c*, stretch blind hem stitching 130*d*, blind hem stitching 130*e*, and/or elastic overlock stitching 130*f*.

Referring again to FIGS. 1 and 2, the exemplary garment 100 is a shirt. The shirt 100 includes a plurality of panels 102. The panels 102 form a torso portion 120, a first arm 122, and a second arm 124. The first arm 122 is joined at an upper end 126 thereof to the torso portion 120. The second arm 124 is joined at an upper end 128 thereof to the torso portion 120. It will be appreciated that the shirt may include one or more further portions 138, such as a collar portion 138 joined to the torso portion 120, a waist portion joined to the torso portion 120, or a wrist portion joined to one of the arms 122, 124. The one or more further portions 138 are be formed from panels 102 (e.g., formed from regular materials not incorporating temperature therapy material). In some examples, the torso portion 120, the first arm 122, and the second arm 124 consist of the panels 102 (e.g., as in the exemplary shirt of FIGS. 1 and 2), optionally with one or more further portions 138.

In some examples, the garment is formed from relatively large panels 102 to extend continuously across a substantial portion of a wearer's body. The exemplary garment 100 of FIG. 2 includes a first panel 102*a* extending at least from a torso right side 142 to a torso left side 144, and the continuous sheet 106 of temperature therapy material in the panel 102*a* also extends at least from the torso right side 142 to the torso left side 144. The exemplary first panel 102*a* of FIG. 2 is a rear torso panel. The exemplary first edge 104*a* of the first panel 102*a* of FIG. 2 is at a torso right side seam 150 and the second edge 104*b* of the first panel 102*a* is at a torso left side seam 152. Optionally, the panel 102*a* extends further than from the torso right side 142 to the torso left side 144, such as also extending around from one of the front and back sides to the other. Optionally, the panel 102*a* forms a sleeve encircling the torso and extending between an upper edge and a lower edge. However, in many embodiments the torso portion 120 includes at least a front panel and a back panel joined together to form the torso portion 120, e.g., for ease of manufacturing.

In some examples, the first panel 102*a* also extends from a lower end 146 of the torso portion 120 to an upper end 148 of the torso portion 120, and the continuous sheet 102 of temperature therapy material in the panel 102*a* also extends from the lower end 146 of the torso portion 120 to the upper end 148 of the torso portion 120. The lower end of the first panel 102*a* may form a bottom edge of the torso portion 120 and/or be joined to a further portion 138 of the garment 100. The upper end of the first panel 102*a* may form an upper edge of the torso portion 120 and/or be joined to a further portion 128 of the garment 100 (e.g., a collar portion).

The garment 100 is a reusable garment. In use, the garment (e.g., the temperature therapy material) is warmed or cooled, then worn by a wearer (e.g., for at least a few minutes), then removed. After the garment is removed, it can again be warmed or cooled, then worn by a wearer, and then removed, and the cycle can continue multiple times. For example, a user may place the garment in a refrigerator on a first day, take the garment out of the refrigerator and wear the garment for five minutes on a second, subsequent day, place the garment in a closet on the second day after wearing the garment, move the garment into the refrigerator on a third, subsequent day, and then later on the third day take the garment out of the refrigerator and wear it for a few minutes.

Figure 5:
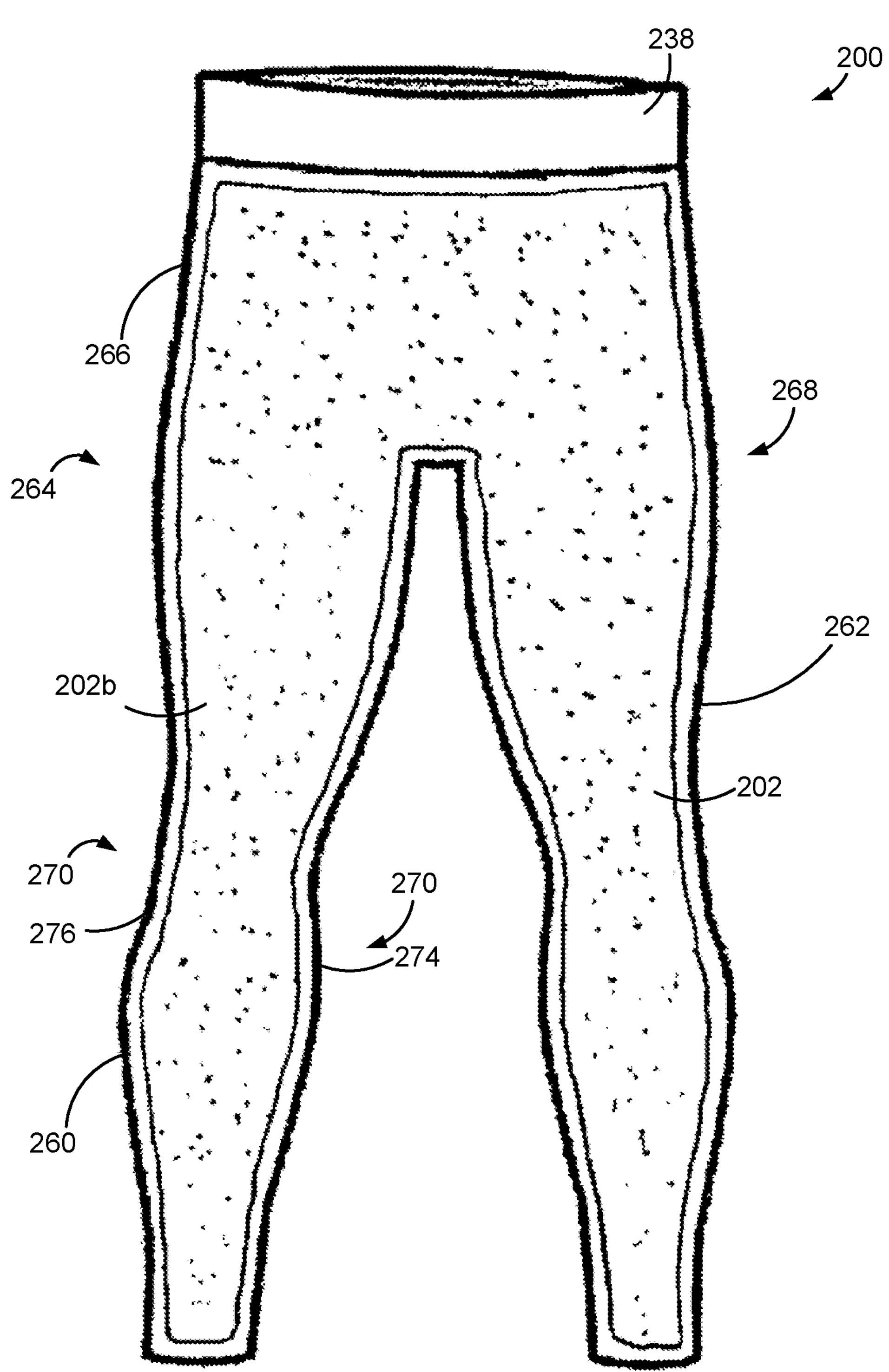
FIG. 5 is a front view of a temperature therapy pants, according to an embodiment.
Figure 6:
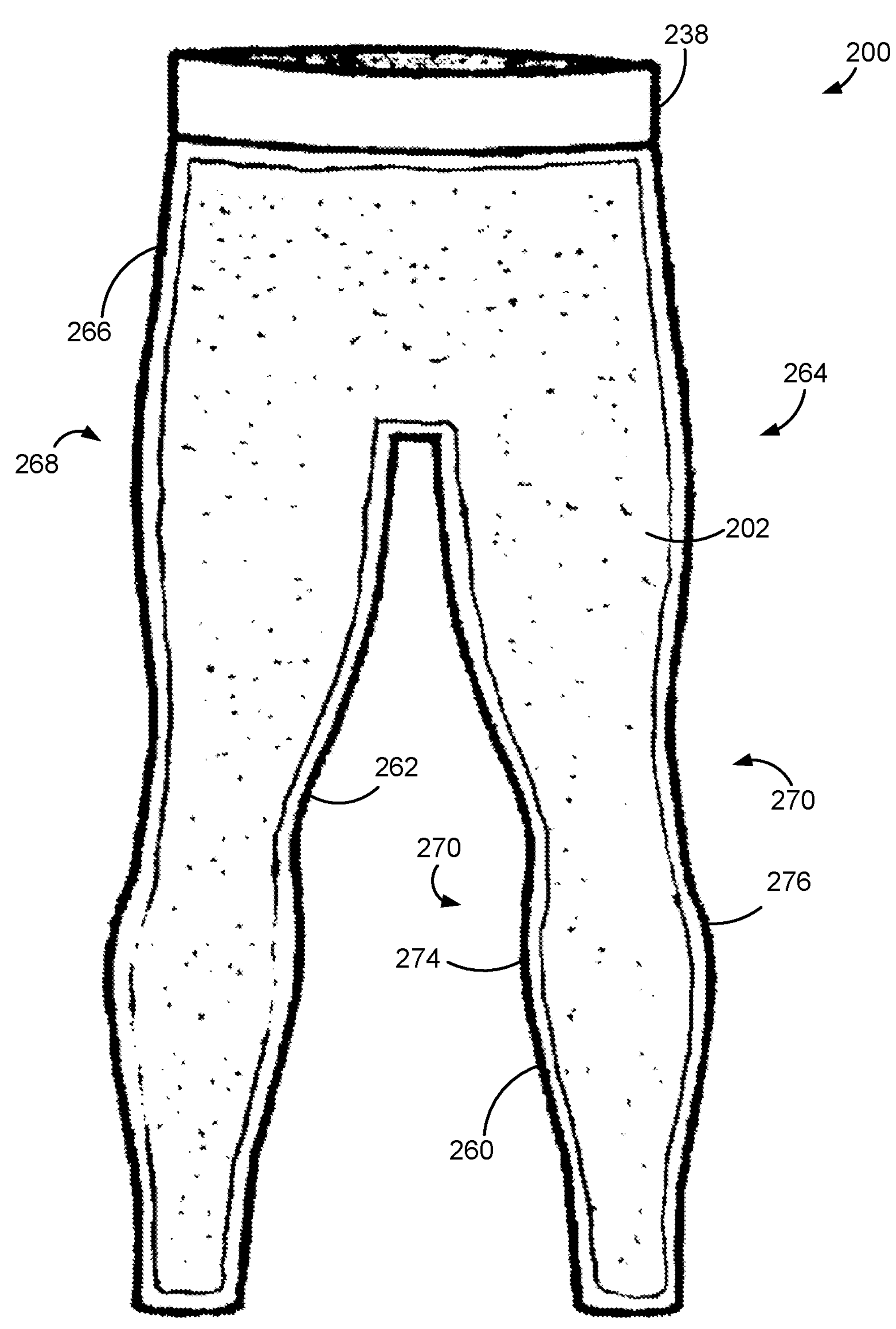
FIG. 6 is a rear view of the temperature therapy pants of FIG. 5.

While the exemplary garment 100 of FIGS. 1 and 2 is a shirt, the garment may take the form of another type of garment. In some examples, the garment 100 is a pair of pants. Referring now to FIGS. 5 and 6, illustrated is an exemplary garment 200 formed as pants. Garment 200 is similar in some respects to garment 100 of FIGS. 1 and 2, and similar features are indicated by similar reference characters incremented by 100.

Garment 200 includes one or more clothing panels 202. The clothing panel 202 is similar to the clothing panel 102, including a sheet of temperature therapy material. The clothing panels 202 form a first leg 260 and a second leg 262. The first leg 260 is joined at an upper end 264 thereof to a waist portion 266. The second leg 262 is joined at an upper end 268 thereof to the waist portion 266. In some examples, the first and second legs 260, 262 consist of the one or more clothing panels 202.

The garment 200 is a compression garment. The exemplary pants is a compression pants sized and shaped to compress the legs of a wearer. Stitching in the garment 200 may be compression stitching, such as to join panels 202 to one another.

Figure 7:
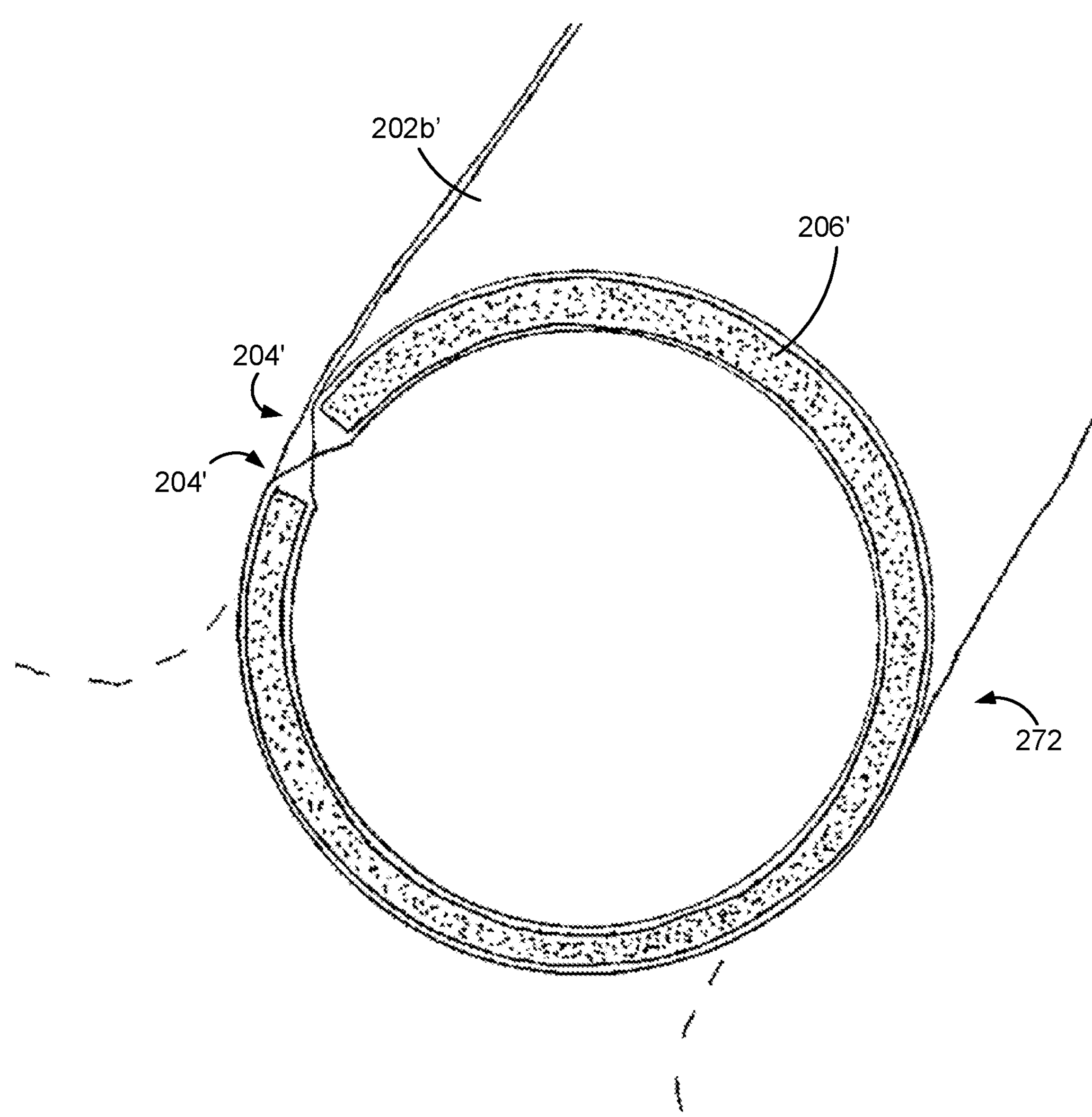
FIG. 7 is a perspective cross sectional view of a clothing panel of another temperature therapy pants; and, FIG. 8 is a flow diagram of a method of temperature therapy, according to an embodiment.

The exemplary garment 200 includes a first panel **202*b*. The first panel 202*b* extends at least from a right side 270 of one of the first and second legs 260, 262 to a left side 272 of the one of the first and second legs, and the continuous sheet of temperature therapy material of the first panel 202*b* also extends at least from the right side 270 of the one of the first and second legs to the left side 272 of the one of the first and second legs. In some examples, the first panel 202*b* extends beyond the first and/or second sides 270, 272, such as forming a circumferentially continuous sleeve to receive a leg therein. In some examples, the sheet of temperature therapy material also forms a circumferentially continuous sleeve. Referring to FIG. 7, the exemplary first panel 202*b*' extends around an interior with opposing edges 204' of the panel 202*b*' joined to one another to form a sleeve in which may be received, e.g., a leg. A continuous sheet 206' of temperature therapy material of the exemplary panel 202*b*' of FIG. 7** also extends around an interior of the sleeve.

However, in some examples, the pants include a plurality of clothing panels 202 joined to one another to form the legs. The exemplary first panel **202*b* of FIGS. 5 and 6 is a front panel, and is joined to one or more additional panels 202 at an inseam 274 and an outseam 276** (e.g., joined to a cooperating back panel at the inseam and at the outseam).

In some examples, the first panel **202*b* also extends at least from a lower end 280 of the one of the first and second legs to the upper end 282 of the one of the first and second legs, and the continuous sheet of temperature therapy material of the first panel also extends at least from the lower end 280 of the one of the first and second legs to the upper end 282 of the one of the first and second legs. The lower end of the first panel 202*b* may form a bottom edge of the leg and/or be joined to a further portion of the garment (e.g., a hem portion). The upper end of the first panel 202*b* may be joined directly to the waist portion 266 or continue through the waist portion 266 and form the upper edge of the pants and/or be joined to a further portion 238 of the garment (e.g., a waistband). In some examples, the waist portion 266 is also formed of the one or more clothing panels 202**.

In some embodiments, more than one garment 100 is provided for use together. In some embodiments, a temperature therapy suit is provided. The suit covers more than 50% of the user's body. In some examples, the suit covers more than 60% of the user's body. The suit includes a shirt and a pair of pants, such as the shirt of FIGS. 1 and 2 and the pants of FIGS. 5 and 6.

Figure 8:
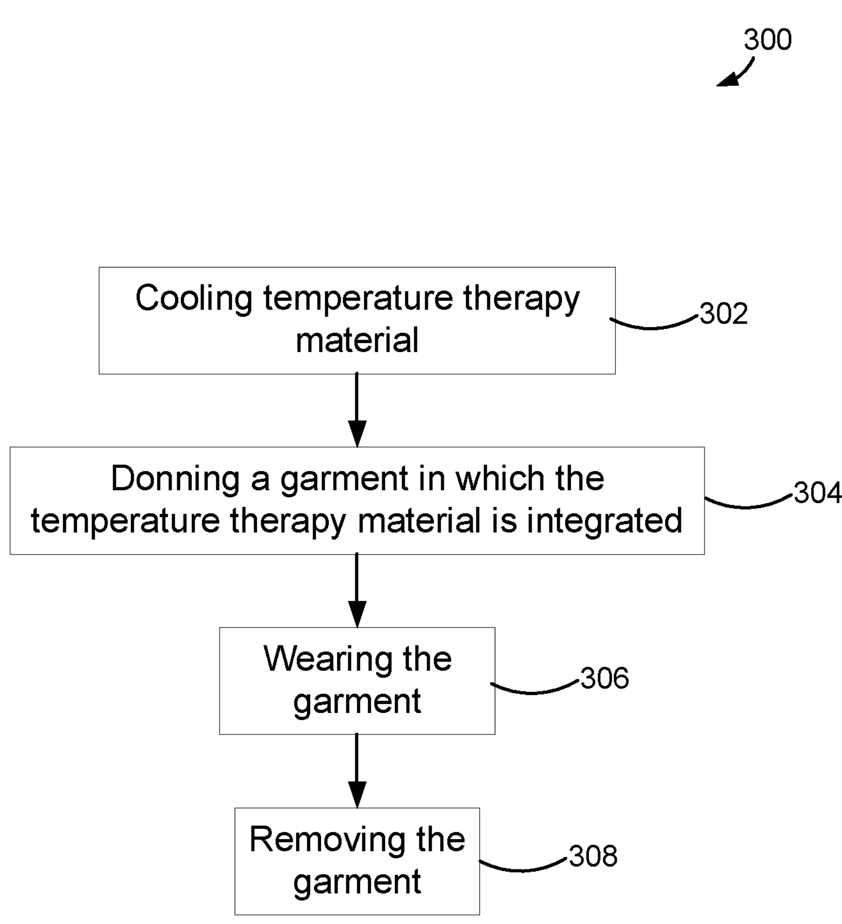

Referring now to FIG. 8, illustrated is an exemplary method of temperature therapy 300. Method 300 includes, at step 302, cooling or warming a temperature therapy material in at least one temperature therapy garment. The at least one temperature therapy garment is formed from one or more clothing panels. Each clothing panel extends from a first edge to a second edge opposite the first edge and includes a continuous sheet of the temperature therapy material extending across the panel from the first edge to the second edge, the temperature therapy material having a gel form within an expected use range. In some examples, the expected use range for cold therapy is any of the ranges described herein, such as at least a temperature range of −20 degrees Celsius to 30 degrees Celsius or 3 degrees Celsius to 20 degrees Celsius. In some examples, the expected use range for hot therapy is any of the ranges described herein, such as at least a temperature range of 20 degrees Celsius to 35 degrees Celsius. In some examples, the garment is the exemplary garment 100 of FIGS. 1 and 2 or the exemplary garment 200 of FIGS. 5 and 6. In some examples, step 302 includes cooling or warming the temperature therapy material in more than one garment. In some examples, the at least one garment is a compression garment sized and shaped to compress an underlying body of a wearer.

At step 304, method 300 includes donning, after cooling or warming the temperature therapy material, the at least one temperature therapy garment whereby the at least one temperature therapy garment overlies at least 30% of a surface area of a wearer's body. In some examples, step 304 includes donning more than one temperature therapy garment. In some examples, step 304 includes donning one or more temperature therapy garments such that the garments overly at least 60% of a surface area of a wearer's body. Method 300 also includes, at step 306, wearing, after donning the at least one temperature therapy garment, the at least one temperature therapy garment for a period of time whereby a skin temperature of the wearer is changed to a target temperature. In some examples, for cold therapy the target temperature is a decreased temperature. The decreased temperature may be less than 30 degrees Celius, less than 27 degrees Celsius, or less than 25 degrees Celsius. In some examples, for hot therapy the target temperature is an increased temperature. The increased temperature may be more than 37 degrees Celius, more than 40 degrees Celsius, or more than 43 degrees Celsius.

At step 308, method 300 includes removing the at least one temperature therapy garment after the skin temperature of the wearer decreases to the decreased temperature.

EXAMPLES

The effects of using cold therapy clothing panels (such as exemplary panel 102 of FIGS. 1 to 3) were compared to the effects of an ice bath. In each cold therapy clothing panel treatment, the cold therapy clothing panels were cooled prior to use in a refrigerator to about −18 degrees Celsius.

Example 1

A subject took a five minute ice bath in the morning using 27 pounds of ice. The subject's skin temperature immediately following the ice bath was measured at between 24 and 25 degrees Celsius. In the afternoon of the same day, the subject placed cold therapy clothing panels on the subject's thighs. The subject's skin temperature immediately following the cold therapy clothing panel treatment was measured at 25 degrees Celsius.

Example 2

On a first day, a subject took a seven minute ice bath using 20 pounds of ice. The subject's skin temperature immediately following the ice bath was measured at between 24 and 26 degrees Celsius.

On a second day, the subject took a five minute cold shower in the morning. The subject's skin temperature immediately following the cold shower was measured at between 28 and 29 degrees Celsius. In the afternoon of the second day, the subject placed cold therapy clothing panels on the subject's thighs for three minutes. The subject's skin temperature immediately following the cold therapy clothing panel treatment measured at between 22 and 23 degrees Celsius.

Example 3

On a first day, a subject took a four minute ice bath using 53 pounds of ice with a water temperature of 9.5 degrees Celsius. The subject's skin temperature immediately following the ice bath was measured at between 22 and 23 degrees Celsius.

On a second day, the subject took a six minute ice bath using 27 pounds of ice with a water temperature of 15 degrees Celsius. The subject's skin temperature immediately following the ice bath was measured at between 24 and 25 degrees Celsius.

On a third day, the subject took a six minute ice bath following a regular temperature shower, the ice bath using 27 pounds of ice and with a water temperature of 15 degrees Celsius. The subject's skin temperature immediately following the ice bath was measured at 24 degrees Celsius.

On a fourth day, the subject took a six minute ice bath following a regular temperature shower, the ice bath using 27 pounds of ice and with a water temperature of 14 degrees Celsius. The subject's skin temperature immediately following the ice bath was measured at between 22 and 23 degrees Celsius.

On a fifth day, the subject took a regular temperature shower and, immediately following the shower, the subject placed cold therapy clothing panels on the subject's thighs and cold therapy clothing panels on the subject's arms for four minutes. The subject's skin temperature immediately following the cold therapy clothing panel treatment was measured at between 22 and 24 degrees Celsius.

The present invention has been described here by way of example only. Various modification and variations may be made to these examples without departing from the scope of the invention, which is limited only by the appended claims.

The invention claimed is:

1. A cold therapy shirt, comprising:

a plurality of clothing panels forming a torso portion and first and second arms, the first and second arms each joined at upper ends thereof to the torso portion, and wherein each clothing panel extends from a first edge to a second edge opposite the first edge and each clothing panel includes an integrated flexible gel sheet to be cooled prior to a user wearing the cold therapy shirt, each integrated flexible gel sheet extending continuously across the clothing panel from the first edge to the second edge, and each integrated flexible gel sheet formed of a cold therapy material having a semi-rigid form throughout a selected temperature use range, and wherein the cold therapy material has a continuous constant thickness and extends continuously across the clothing panel from the first edge to the second edge, and the cold therapy material is soft throughout the selected temperature use range.

2. The cold therapy shirt of claim 1, wherein the cold therapy material is a hydrogel.

3. The cold therapy shirt of claim 1, wherein the selected temperature use range includes a range of 3 degrees Celsius to 20 degrees Celsius.

4. The cold therapy shirt of claim 1, wherein the plurality of clothing panels includes a first panel extending at least from a torso right side to a torso left side, and the continuous sheet of cold therapy material of the first panel also extends at least from the torso right side to the torso left side and has the generally constant thickness of the cold therapy material across the first panel from the torso right side to the torso left side.

5. The cold therapy shirt of claim 4, wherein the first panel also extends at least from a lower end of the torso portion to an upper end of the torso portion, and the continuous sheet of cold therapy material of the first panel also extends at least from the lower end of the torso portion to the upper end of the torso portion and has the generally constant thickness of the cold therapy material across the first panel from the lower end of the torso portion to the upper end of the torso portion.

6. The cold therapy shirt of claim 5, wherein the first panel is a rear torso panel and the first edge is at a torso right side seam and the second edge is at a torso left side seam.

7. The cold therapy shirt of claim 1, wherein each panel comprises the sheet of cold therapy material enclosed between layers of fabric.

8. The cold therapy shirt of claim 1, further comprising stretch stitching joining the plurality of clothing panels to one another, and the cold therapy shirt is sized and shaped to compress a torso and arms of the user.

9. The cold therapy shirt of claim 7, wherein the sheet of cold therapy material has a sticky outer surface directly overlaid by the layers of fabric.

10. The cold therapy shirt of claim 7, wherein the layers of fabric include an inner layer of fabric directly overlying an inner face of the sheet and an outer layer of fabric directly overlying an outer face of the sheet, and the outer layer is attached to the inner layer of fabric to encase the sheet.

11. The cold therapy shirt of claim 10, wherein the sheet has an inner face and an opposite outer face, and the inner face is covered only by a single layer of fabric and the outer face is covered only by a single layer of fabric.

12. The cold therapy shirt of claim 1, wherein each sheet of the cold therapy material has an inner face and an opposite outer face and is encased by a cover, the cover includes only a single layer of fabric over the outer face and only a single layer of fabric between the inner face and an interior of the garment.

13. The cold therapy shirt of claim 1, wherein the plurality of clothing panels includes a first panel which extends around an interior with opposing edges of the panel joined to one another to form a sleeve, the sheet of temperature therapy material of the first panel also extends continuously around the interior of the sleeve from one of the opposing edge of the panel to the other of the opposing edge of the panel.

14. The cold therapy shirt of claim 1, wherein the sheet of cold therapy material of each clothing panel has an inner face extending continuously across the clothing panel from the first edge to the second edge and an outer face opposite the inner face and extending continuously across the clothing panel from the first edge to the second edge, and wherein the sheet of cold therapy material, including the inner and outer faces, is free of voids or breaks in the cold therapy material between the first edge and the second edge.

15. Use of the cold therapy shirt of claim 1 to overly at least 30% of a user's body in a cold therapy treatment to activate brown fat.

* * * * *